(12) United States Patent
Yokota

(10) Patent No.: US 10,274,422 B2
(45) Date of Patent: Apr. 30, 2019

(54) GAS ANALYSIS APPARATUS AND GAS ANALYSIS METHOD

(71) Applicant: HORIBA, Ltd., Kyoto (JP)

(72) Inventor: Yoshihiro Yokota, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 15/817,556

(22) Filed: Nov. 20, 2017

(65) Prior Publication Data

US 2018/0149586 A1    May 31, 2018

(30) Foreign Application Priority Data

Nov. 29, 2016 (JP) .................................. 2016-231473

(51) Int. Cl.
    *G01N 21/3504* (2014.01)
    *G01N 33/00* (2006.01)
    (Continued)

(52) U.S. Cl.
    CPC ....... *G01N 21/3504* (2013.01); *G01N 21/274* (2013.01); *G01N 33/004* (2013.01);
    (Continued)

(58) Field of Classification Search
    CPC ........... G01N 27/4175; G01N 33/0037; G01N 2021/3133; G01N 2021/3174;
    (Continued)

(56) References Cited

U.S. PATENT DOCUMENTS 5,559,333 A * 9/1996 Araya ................ G01N 21/3504
    250/339.13
5,986,757 A * 11/1999 Seltzer .................... G01J 3/443
    356/307

(Continued)

FOREIGN PATENT DOCUMENTS

JP      10-123052 A    5/1998
JP      2000-356589 A    12/2000

OTHER PUBLICATIONS

EESR dated Jan. 30, 2018 issued for European Patent Application No. 17 203 886.1, 10 pgs.

(Continued)

*Primary Examiner* — Taeho Jo
(74) *Attorney, Agent, or Firm* — Brooks Kushman P.C.

(57) ABSTRACT

The present invention is one adapted to correct the effect of a second gas component on a first gas component in real time even when the concentration of the second gas component as a coexistent component varies every moment, and includes: a first gas analysis part adapted to measure the concentration of the first gas component contained in sample gas; a second gas analysis part adapted to measure the concentration of the second gas component contained in the sample gas; a correction coefficient storage part adapted to store a correction coefficient for correcting the effect of the second gas component on the first gas component; and a concentration correction part adapted to correct the first gas component concentration on the basis of the correction coefficient, the second gas component concentration of (Continued)

calibration gas used for calibrating the first gas analysis part, and the second gas component concentration.

7 Claims, 4 Drawing Sheets

(51) Int. Cl.
 *G01N 21/27* (2006.01)
 *G01N 21/35* (2014.01)
(52) U.S. Cl.
 CPC ............ *G01N 2021/3545* (2013.01); *G01N 2021/3595* (2013.01)
(58) Field of Classification Search
 CPC ............ G01N 21/031; G01N 21/274; G01N 21/3504; G01N 33/004; G01N 2021/3545; G01N 2021/3595
 USPC ...................................................... 250/341.1
 See application file for complete search history.

(56) References Cited

U.S. PATENT DOCUMENTS

| | | | | |
|---|---|---|---|---|
| 6,147,351 A | * | 11/2000 | Huiku | G01N 21/0303 250/343 |
| 6,422,056 B1 | * | 7/2002 | Miyai | G01N 21/274 73/1.06 |
| 7,217,121 B2 | * | 5/2007 | Thomson | B08B 7/00 250/339.01 |
| 7,377,150 B2 | * | 5/2008 | Tezuka | H01M 8/0618 422/54 |
| 8,866,085 B1 | * | 10/2014 | Wong | G01N 21/3504 250/341.1 |
| 9,823,181 B2 | * | 11/2017 | Hayashi | G01N 21/05 |
| 2002/0130053 A1 | * | 9/2002 | Ando | F01N 3/0842 205/781 |
| 2003/0042151 A1 | * | 3/2003 | Ando | F01N 3/0842 205/781 |
| 2003/0071218 A1 | | 4/2003 | Nakamura et al. | |
| 2008/0111077 A1 | * | 5/2008 | Miller | G01N 21/39 250/339.07 |
| 2008/0179530 A1 | * | 7/2008 | Liu | G01N 21/274 250/343 |
| 2009/0039284 A1 | * | 2/2009 | Goto | G01J 3/02 250/432 R |
| 2009/0198474 A1 | * | 8/2009 | Fritz | G01M 15/06 702/183 |
| 2009/0213380 A1 | * | 8/2009 | Appel | G01N 21/274 356/437 |
| 2011/0307217 A1 | * | 12/2011 | Fritz | G01M 15/06 702/183 |
| 2013/0118229 A1 | * | 5/2013 | Okada | G01M 15/10 73/23.31 |
| 2014/0136136 A1 | * | 5/2014 | Onogi | G01N 27/4175 702/98 |
| 2014/0338540 A1 | * | 11/2014 | Yoshimura | G01N 1/2252 96/413 |
| 2015/0330868 A1 | * | 11/2015 | Fukami | G01N 1/2252 73/23.31 |

OTHER PUBLICATIONS

Severinghaus J.W. et al., Correction Factors for Infrared Carbon Dioxide Pressure Broadening by Nitrogen, Nitrous Oxide and Cyclopropane, Anesthesiology, Jan. 1, 1961, p. 429-432, vol. 22.

* cited by examiner

GAS ANALYSIS APPARATUS AND GAS ANALYSIS METHOD

CROSS-REFERENCE TO RELATED APPLICATION

This application claims priority to JP Application No. 2016-231473, filed Nov. 29, 2016, the disclosure of which is incorporated in its entirety by reference herein.

TECHNICAL FIELD

The present invention relates to a gas analysis apparatus and a gas analysis method capable of correcting the effects of gas, such as a coexistent effect and an interference effect.

BACKGROUND ART

As a gas analysis apparatus adapted to measure the concentration of a measurement target component contained in sample gas such as an exhaust gas of an internal combustion engine, there is one using an infrared absorption method.

It is known that when measuring the concentration of a measurement target component (e.g., carbon monoxide (CO)) using the infrared absorption method, another gas component (e.g., carbon dioxide ($CO_2$)) coexistent with the measurement target component in sample gas exerts a coexistent effect.

The coexistent effect is considered to occur due to the fact (broadening phenomenon) that wavenumbers are shifted by the intermolecular interaction of the coexistent component to thereby broaden the linewidth of the infrared absorption spectrum of the measurement target component broadens, and consequently the infrared spectrum changes into a broad shape.

In the past, as a gas analysis apparatus capable of removing the coexistent effect, there has been a gas analysis apparatus disclosed in Patent Literature 1. This gas analysis apparatus determines a sensitivity adjustment coefficient using the average concentration of a coexistent component in an actual sample for calibration.

However, since the gas analysis apparatus determines a sensitivity adjustment coefficient using the average concentration of a coexistent component in an actual sample for calibration, when measuring gas having different coexistent component concentration from that at the time of the calibration, an error due to the coexistent effect occurs. Further, in the case of measurement during which coexistent component concentration changes every moment as well, the coexistent effect of a coexistent component cannot be exactly eliminated.

CITATION LIST

Patent Literature

Patent Literature 1: Japanese Unexamined Patent Publication JP-A 2000-356589

SUMMARY OF INVENTION

Technical Problem

Therefore, the present invention is made in order to solve the above-described problems, and a main object thereof is to, even when the concentration of a second gas component as a coexistent component varies, accurately correct the effect of the second gas component on a first gas component in real time.

Solution to Problem

That is, a gas analysis apparatus according to the present invention includes: a first gas analysis part adapted to measure the concentration of a first gas component contained in sample gas; a second gas analysis part adapted to measure the concentration of a second gas component contained in the sample gas; a correction coefficient storage part adapted to store a correction coefficient for correcting the effect of the second gas component on the first gas component; and a concentration correction part adapted to correct the first gas component concentration obtained by the first gas analysis part on the basis of the correction coefficient, second gas component concentration of calibration gas used for calibrating the first gas analysis part, and the second gas component concentration obtained by the second gas analysis part.

Also, a gas analysis method according to the present invention is a gas analysis method using a first gas analysis part adapted to measure the concentration of a first gas component contained in sample gas and a second gas analysis part adapted to measure the concentration of a second gas component contained in the sample gas, and the gas analysis method corrects the first gas component concentration obtained by the first gas analysis part on the basis of a correction coefficient for correcting the effect of the second gas component on the first gas component, second gas component concentration of calibration gas used for calibrating the first gas analysis part, and the second gas component concentration obtained by the second gas analysis part.

Such gas analysis apparatus and method correct the first gas component concentration obtained by the first gas analysis part on the basis of the correction coefficient, the second gas component concentration of the calibration gas used for calibrating the first gas analysis part, and the second gas component concentration obtained by the second gas analysis part, and can therefore accurately correct the effect of the second gas component on the first gas component in real time even when the concentration of the second gas component as a coexistent component varies. In addition, even when using mixed gas containing at least the first gas component and the second gas component as the calibration gas for the first gas analysis part, the effect of the second gas component on the first gas component can be accurately corrected in real time.

As a specific embodiment of the correction in the gas analysis apparatus, it is conceivable that the concentration correction part corrects the first gas component concentration on the basis of the correction coefficient and the difference between the second gas component concentration of the calibration gas and the second gas component concentration obtained by the second gas analysis part.

As a specific embodiment of the correction in the gas analysis apparatus, it is preferable that the gas analysis apparatus further includes a correction coefficient changing part adapted to change the correction coefficient on the basis of the second gas component concentration of the calibration gas used for calibrating the first gas analysis part, and the concentration correction part corrects the first gas component concentration obtained by the first gas analysis part with use of a correction coefficient after the change by the correction coefficient changing part and the second gas component concentration obtained by the second gas analysis part.

It is preferable that the correction coefficient indicates the relationship between second gas component concentration and the relative error of first gas component concentration at the second gas component concentration, and the correction coefficient changing part changes the correction coefficient on the basis of the difference between second gas component concentration at which the relative error of the first gas component concentration is zero under the condition of the correction coefficient and the second gas component concentration of the calibration gas used for calibrating the first gas analysis part.

As a specific changing method to be employed by the correction coefficient changing part, it is conceivable that the correction coefficient changing part shifts the correction coefficient so as to make second gas component concentration at which the relative error of the first gas component concentration is zero equal to the second gas component concentration of the calibration gas.

It is preferable that the first gas analysis part and the second gas analysis part include a detector using an NDIR method. In particular, when the first gas analysis part and the second gas analysis part are configured to include one NDIR detector having a single cell, the length of the cell is specified. As a result, a usable wavelength is limited and it is likely to exert effects such as a coexistent effect. In the case of such a configuration, the effect of the present invention is notably produced.

When measurement target components in the sample gas are carbon monoxide (CO) and carbon dioxide ($CO_2$), the coexistent effect of the carbon dioxide ($CO_2$) on the carbon monoxide (CO) causes a measurement error. In this case, the first gas component is the carbon oxide (CO) and the second gas component is the carbon dioxide ($CO_2$).

Advantageous Effects of Invention

According to the present invention configured as described above, even when the concentration of the second gas component as a coexistent component varies every moment, the effect of the second gas component on the first gas component can be corrected in real time.

DESCRIPTION OF EMBODIMENTS

In the following, one embodiment of a gas analysis apparatus according to the present invention will be described with reference to the drawings.
<Apparatus Configuration>
A gas analysis apparatus 100 of the present embodiment is one adapted to analyze multiple gas components contained in exhaust gas discharged from an exhaust gas source such as an engine. In the present embodiment, the gas analysis apparatus 100 is one that, using a non-dispersive infrared absorption method (NDIR method), simultaneously measures the multicomponent gas containing carbon monoxide (CO) as a first gas component and carbon dioxide ($CO_2$) as a second gas component both contained in engine exhaust gas. The gas analysis apparatus 100 does not have to be one adapted to simultaneously measure the multicomponent gas but may be one using an optical absorption method other than the NDIR method, such as an FTIR method.

Note that $CO_2$ as the second gas component exerts a coexistent effect on CO as the first gas component in the NDIR method. That is, the infrared absorption spectrum of CO as the first gas component broadens because wavenumbers are shifted by the intermolecular interaction of $CO_2$.

Figure 1:
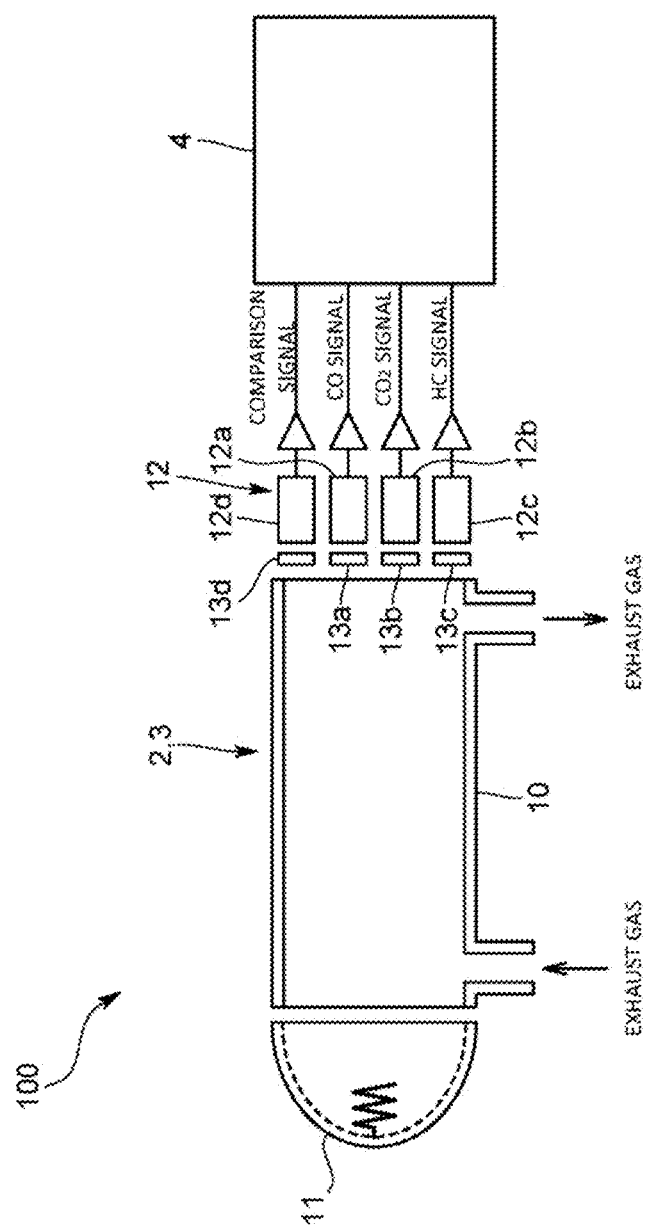
FIG. 1 is a schematic diagram illustrating the configuration of a gas analysis apparatus according to the present invention.

Specifically, as illustrated in FIG. 1, the gas analysis apparatus 100 includes: a first gas analysis part 2 adapted to continuously measure the concentration of CO contained in the engine exhaust gas; a second gas analysis part 3 adapted to continuously measure the concentration of $CO_2$ contained in the engine exhaust gas; and a calculation device 4 adapted to acquire outputs from the respective analysis parts 2 and 3 and calculate the concentrations of CO and $CO_2$ contained in the engine exhaust gas.

The first gas analysis part 2 and the second gas analysis part 3 are ones including NDIR detectors, and configured using a single shared cell. Specifically, the analysis parts 2 and 3 include: the measurement cell 10 into/from which the engine exhaust gas is introduced/led out; an infrared ray irradiation part 11 adapted to irradiate the measurement cell 10 with infrared light, such as an infrared light source; and the infrared detectors 12 adapted to detect infrared rays having passed through the measurement cell 10.

The infrared detectors 12 in the present embodiment are pyroelectric infrared detectors, and include a detector 12a for CO measurement and a detector 12b for $CO_2$ measurement. In addition, the infrared detectors 12 also include a detector 12c for hydrocarbon (HC) measurement and a detector 12d for a comparison signal. Between the respective detectors 12a to 12d and the measurement cell 10, optical filters 13a to 13d are provided, and the respective optical filters 13a to 13d have different transmission characteristics, and correspond to absorption wavelengths of CO, $CO_2$, and HC, and a reference wavelength at which any of them does not cause absorption. Note that as the infrared detectors 12, in addition to the pyroelectric infrared detectors, pneumatic cell infrared detectors, detectors using lead selenide, thermopile detectors, or the like can be used.

The calculation device 4 is a dedicated or general-purpose computer including a CPU, a memory, an input/output interface, an AD converter, and the like, and in accordance with an analysis program stored in the memory, calculates the CO concentration, the $CO_2$ concentration, and HC concentration.

Specifically, the calculation device 4 is one adapted to acquire output signals (light intensity signals) from the infrared detectors 12 constituting the first and second gas analyzers 2 and 3, and using absorption spectra obtained from the light intensity signals from the respective detectors 12a to 12d, calculate the CO concentration, $CO_2$ concentration, and HC concentration.

Figure 2:
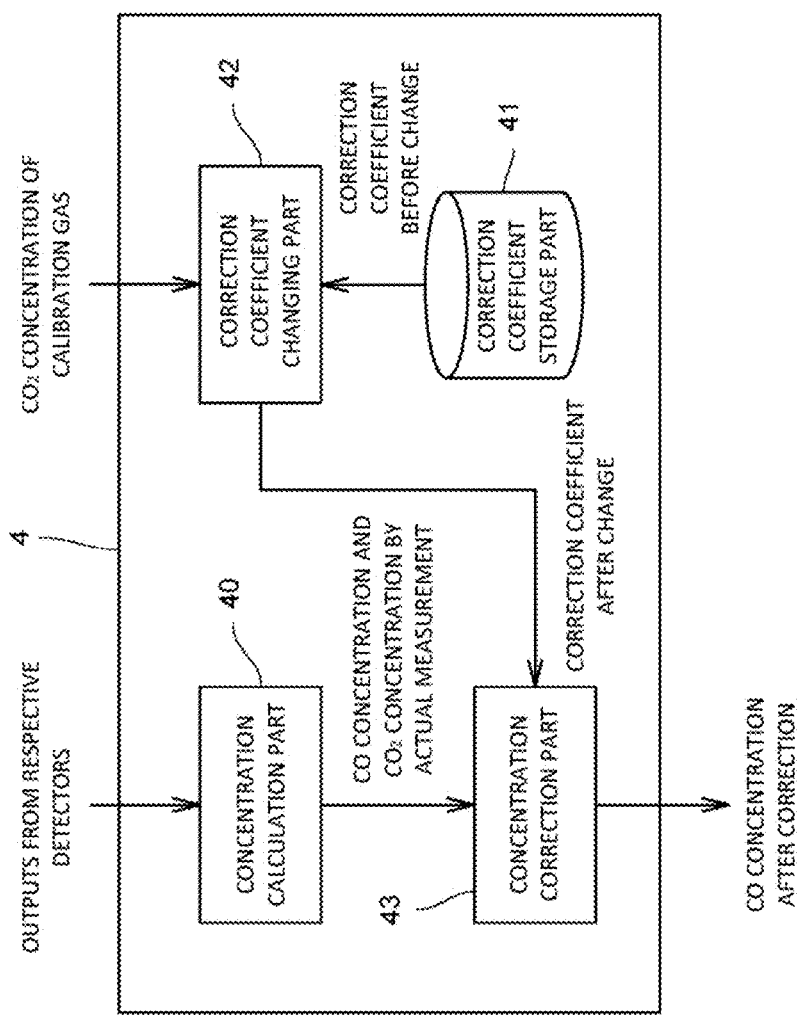
FIG. 2 is a functional configuration diagram of a calculation device in the same embodiment.

In addition, the calculation device 4 has a function of correcting the coexistent effect of the $CO_2$ as the second gas component on the CO as the first gas component, and in accordance with the analysis program stored in the memory, as illustrated in FIG. 2, fulfills functions as a concentration calculation part 40, a correction coefficient storage part 41, a correction coefficient changing part 42, a concentration correction part 43, and the like.

The concentration calculation part 40 is one adapted to calculate the CO concentration, $CO_2$ concentration, and HC concentration using the absorption spectra obtained from the light intensity signals from the respective detectors 12a to 12d.

The correction coefficient storage part 41 is one adapted to store a correction coefficient for correcting the coexistent effect of the second gas component on the first gas component. Correction coefficient data indicating the correction coefficient is preliminarily inputted to the correction coefficient storage part 41 before product shipment or before product operation.

Figure 3:
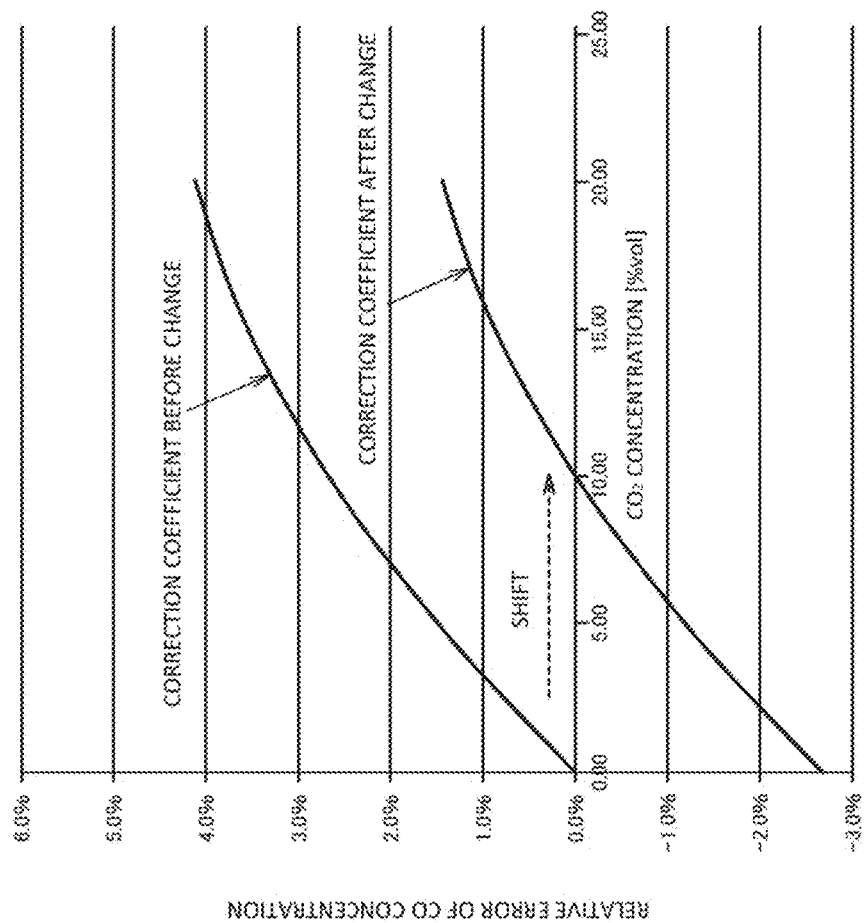
FIG. 3 is a diagram illustrating relational expressions representing correction coefficients before and after change in the same embodiment.

Note that as illustrated in FIG. 3, the correction coefficient is one indicating the relationship between $CO_2$ concentration and the relative error of CO concentration at the $CO_2$ concentration. The saving format of the correction coefficient may be a function format indicating the relationship, or a table format such as a lookup table.

Also, the relative error of CO concentration at the $CO_2$ concentration refers to a ratio of an error to CO concentration (exact value) in the absence of the coexistent effect of $CO_2$. The error is represented by the difference between the CO concentration in the absence of the coexistent effect of $CO_2$ and the CO concentration in the presence of the coexistent effect of $CO_2$.

Relative error=([CO concentration_under coexistent effect]−[CO concentration_not under coexistent effect])/[CO concentration_not under coexistent effect]×100%

The correction coefficient changing part 42 is one adapted to change the correction coefficient on the basis of second gas component concentration of calibration gas used for calibrating the first gas analysis part 2. Note that the infrared detectors 12 including the first gas analysis part 2 in the present embodiment are calibrated using mixed gas of a known concentration of CO and a known concentration of $CO_2$ as the calibration gas. Also, data on the second gas component concentration of the calibration gas used for calibrating the first gas analysis part 2 is stored in the correction coefficient storage part 41 or another data storage part.

For example, when the correction coefficient is one indicating that the relative error of CO concentration at a $CO_2$ concentration of 0 (zero) is zero, the correction coefficient changing part 42 changes the correction coefficient in the following manner using the $CO_2$ concentration of the calibration gas used for calibrating the first gas analysis part 2 as a parameter.

When mixed gas of a known concentration of CO and a known concentration (e.g., 10% vol) of $CO_2$ is used for calibrating the first gas analysis part 2 as the calibration gas, the calibration is performed such that the relative error becomes zero at the known $CO_2$ concentration (10% vol). Accordingly, the correction coefficient changing part 42 changes the correction coefficient on the basis of the difference between the $CO_2$ concentration (0% vol) at which the relative error of CO concentration is zero under the condition of the concentration coefficient and the $CO_2$ concentration (10% vol) of the calibration gas used for calibrating the first gas analysis part 2. That is, the correction coefficient changing part 42 shifts and changes the correction coefficient such that at the $CO_2$ concentration of the calibration gas used for the calibration, the relative error of the CO concentration becomes zero (see FIG. 3). Note that the $CO_2$ concentration (0% vol) used for changing the correction coefficient, at which the relative error is zero, may be the $CO_2$ concentration (0% vol) at which the relative error is within a predetermined range. The predetermined range is one selected by a user.

For example, when under the condition of a correction coefficient before change, the relative error of CO at a $CO_2$ concentration of 0% vol is 0%, and the relative error of CO at a $CO_2$ concentration of 10% vol is 2.65%, under the condition of a correction coefficient after the change, the relative error of CO at a $CO_2$ concentration of 0% vol is −2.65%, and the relative error of CO at a $CO_2$ concentration of 10% vol is 0%.

The concentration correction part 43 is one adapted to, using the correction coefficient after the change by the correction coefficient changing part 42 and the $CO_2$ concentration calculated by the concentration calculation part 40 using the light intensity signals from the second gas analysis part 3, correct the CO concentration calculated by the concentration calculation part 40 using the light intensity signals from the first gas analysis part 2.

Specifically, the calculation device 4 corrects the CO concentration on the basis of the functions of the correction coefficient changing part 42 and concentration correction part 43 in accordance with the following expression.

$C(CO)\_corr = C(CO)/(1+f(C(C_2)))$

Here, $f(C(CO_2))$ represents a function (the correction coefficient after the correction) indicating the relative error of the CO concentration, and $f(C(CO_2))=K_1 \times C(CO_2) \times C(CO_2)+K_2 \times C(CO_2)-\{K_1 \times C(C_2\_span) \times C(CO_2\_span)+K_2 \times C(CO_2\_span)\}$ C(CO)_corr: CO concentration [% vol] at the time of actual measurement after the correction C(CO): the CO concentration [% vol] at the time of actual measurement before the correction $C(CO_2)$: the $CO_2$ concentration [% vol] at the time of actual measurement $C(CO_2\_span)$: Coexistent $CO_2$ concentration [% vol] at the time of span calibration of the CO meter $K_1$, $K_2$: Coefficients obtainable by experiment (in the present embodiment, coefficients when the relationship between $CO_2$ concentration and the relative error of CO concentration is approximated to a quadratic curve).

Figure 4:
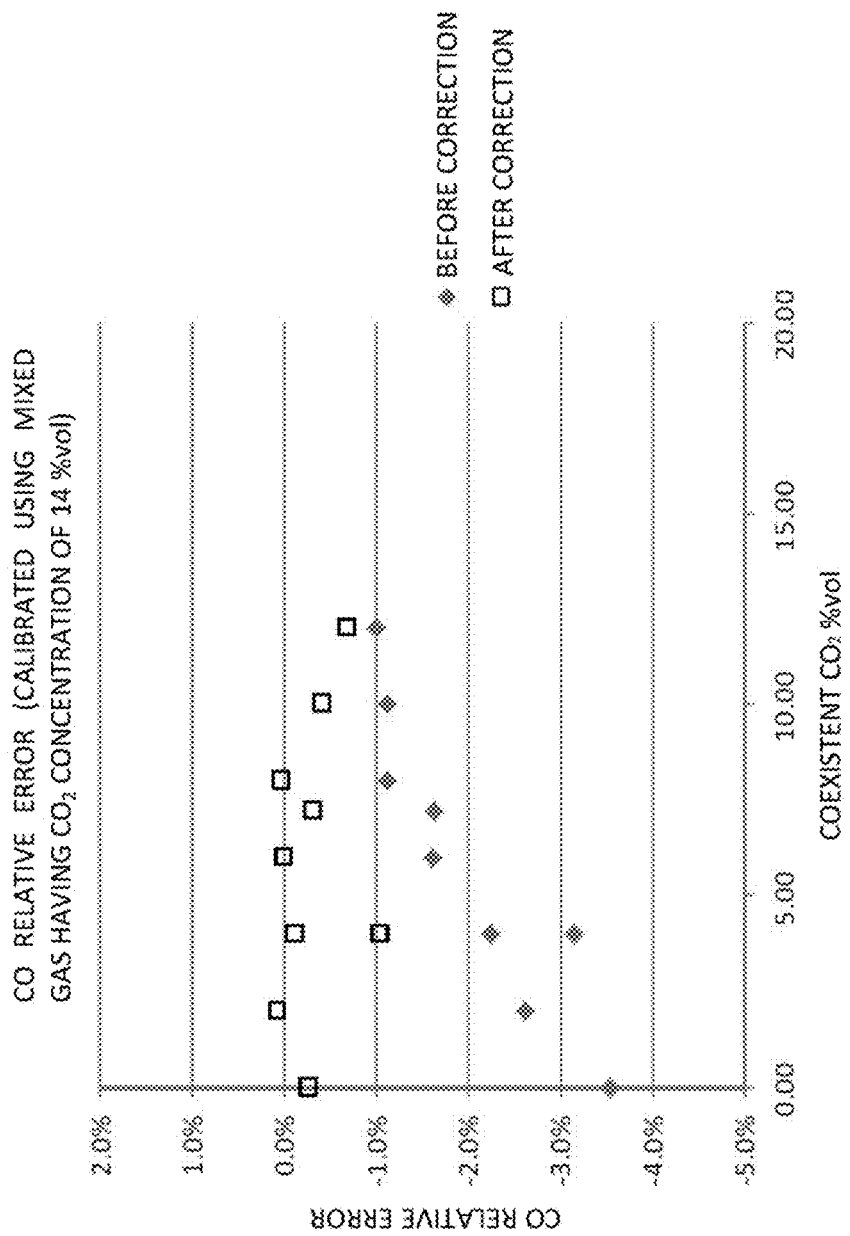
FIG. 4 is a diagram illustrating the relative errors of CO concentration before and after correction in the same embodiment.

FIG. 4 illustrates the relative errors of CO concentration before and after correction obtained when the span calibration of the NDIR detectors were performed using mixed gas having a $CO_2$ concentration of 14% vol as the calibration gas.

As can be seen from FIG. 4, it turns out that correcting the coexistent effect in accordance with the present embodiment allows the relative error of CO concentration after the correction to fall within a range of ±1%.

Effects of the Present Embodiment

The gas analysis apparatus 100 according to the present embodiment configured as described above corrects CO concentration obtained by the first gas analysis part 2 on the basis of a correction coefficient after change by the correction coefficient changing part 42 and $CO_2$ concentration at the time of actual measurement obtained by the second gas analysis part 3, and can therefore accurately correct the coexistent effect of $CO_2$ on CO in real time even when the concentration of $CO_2$ as a coexistent component varies. Note that when using the infrared detectors 12, an interference effect may be caused by the superposition between a $CO_2$ absorption spectrum and a CO absorption spectrum; however, the interference effect is small as compared with the above-described coexistence effect. In order to more accurately measure CO concentration, the interference effect of $CO_2$ on CO may be further corrected in addition to the present embodiment. The interference effect can be corrected using a similar method to that for the coexistence effect by storing a correction coefficient for interference effect correction in the correction coefficient storage part 41.

Other Embodiments

Note that the present embodiment is not limited to the above-described embodiment.

For example, the above-described embodiment is one such that the calculation device 4 includes the correction coefficient changing part 42 and the correction coefficient changing part 42 changes a correction coefficient. However, without changing a correction coefficient, the concentration correction part 43 may correct first gas component concentration using as a parameter the difference between second gas component concentration at which the relative error of the first gas component concentration is zero under the condition of the correction coefficient and second gas component concentration of a calibration gas used for calibrating the first gas analysis part 2. That is, the concentration correction part 43 may be adapted to correct the first gas component concentration obtained by the first gas analysis part 2 on the basis of the unchanged correction coefficient and second gas component concentration obtained by the second gas analysis part 3, and further correct the corrected first gas component concentration on the basis of the difference between the second gas component concentration at which the relative error of the first gas component concentration is zero under the condition of the correction coefficient and the second gas component concentration of the calibration gas used for calibrating the first gas analysis part 2.

For example, when the first gas component concentration obtained by the first gas analysis part 2 is 5% vol and the second gas component concentration obtained by the second gas analysis part 3 is 6% vol, the concentration correction part 43 obtains a relative error using the correction coefficient (e.g., the correction coefficient before the change in the above-described embodiment). In this case, the relative error is approximately +2%. Then, the concentration correction part corrects the first gas component concentration (5% vol) using the relative error (approximately 2%). Subsequently, the concentration correction part 43 further corrects the corrected first gas component concentration (approximately 4.9%) using a change in relative error (a shift amount: −2.65%) under the condition of the correction coefficient shifted on the basis of the difference between the second gas component concentration (0% vol) at which the relative error of the first gas component concentration is zero under the condition of the correction coefficient and the second gas component concentration (e.g., 10% vol) of the calibration gas used for calibrating the first gas analysis part 2. In this case, the further corrected first gas component concentration is approximately 5.37% vol.

Also, the above-described embodiment is one adapted to analyze the engine exhaust gas, but besides may be adapted to analyze sample gas such as environmental gas.

Further, in the above-described embodiment, the first gas analysis part 2 and the second gas analysis part 3 are configured using the single cell, but may be respectively configured as single component meters.

In addition, the above-described embodiment is one adapted to correct the coexistent effect of $CO_2$ on CO between the two components (CO and $CO_2$). However, the present invention may be one adapted to correct the coexistent effect of CO on $CO_2$, correct the coexistent effect between other two components (e.g., two components selected from $CO_2$, $H_2O$, HC, NO, $SO_2$ or the like), or correct the coexistent effect among three components or more (three components or more selected from CO, $CO_2$, $H_2O$, HC, NO, $SO_2$ or the like).

Still in addition, the correction coefficient in the above-described embodiment indicates that at a $CO_2$ concentration of 0% vol, the relative error of CO is 0%, but may be one indicating that at another $CO_2$ concentration, the relative error of CO is 0%.

Yet in addition, the present invention may be one such that without obtaining a correction coefficient after change by the correction coefficient changing part, a correction coefficient preliminarily shifted on the basis of second gas component concentration of a calibration gas is stored in the correction coefficient storage part 41, and the concentration correction part uses the changed correction coefficient stored in the correction coefficient storage part 41.

The gas analysis apparatus may be configured as a vehicle-mounted type that is mounted in a vehicle, and analyzes exhaust gas discharged from an exhaust pipe of the vehicle in running. In the vehicle-mounted gas analysis apparatus as well, calibration is performed using mixed gas of known concentrations of CO, $CO_2$, propane, and the like as calibration gas. Also, the gas analysis apparatus may be adapted to include a moisture meter and correct CO concentration or $CO_2$ concentration using $H_2O$ concentration obtained by the moisture meter.

The above-described embodiment is one adapted to correct the coexistent effect of $CO_2$ on CO, but may be one adapted to correct an interference effect instead of the coexistent effect. The interference effect can also be corrected using a similar method to that for the coexistence effect by storing a correction coefficient for interference effect correction in the correction coefficient storage part 41.

Besides, it goes without saying that the present invention is not limited to any of the above-described embodiment and variations, but can be variously modified without departing from the scope thereof.

REFERENCE SIGNS LIST

100: Gas analysis apparatus
2: First gas analysis part
3: Second gas analysis part
4: Calculation device
41: Correction coefficient storage part
42: Correction coefficient changing part
43: Concentration correction part

The invention claimed is:
1. A gas analysis apparatus comprising:
a first gas analysis part adapted to measure concentration of a first gas component in sample gas;
a second gas analysis part adapted to measure concentration of a second gas component contained in the sample gas, wherein the first gas analysis part is calibrated with use of mixed gas containing known concentrations of the first gas component and the second gas component;
a correction coefficient storage part adapted to store a correction coefficient for correcting error in measured concentration of the first gas component in the sample gas due to presence of the second gas component in the sample gas; and a concentration correction part adapted to correct, as the concentration of the second gas component in the sample gas varies, the error in the measured concentration of the first gas component on a basis of the correction coefficient, the known concentration of the second gas component in the mixed gas, and the measured concentration of the second gas component obtained by the second gas analysis part.

2. The gas analysis apparatus according to claim 1, wherein
the concentration correction part corrects the error in the measured concentration of the first gas component further on a basis of a difference between the known concentration of the second gas component contained in the mixed gas and the measured concentration of the second gas component in the sample gas.

3. The gas analysis apparatus according to claim 1, wherein
the correction coefficient indicates a relationship between a given concentration of the second gas component and a relative error of the concentration of the first gas component at the given concentration of the second gas component,
the gas analysis apparatus further comprising a correction coefficient changing part adapted to shift and change the correction coefficient to make the concentration of the second gas component at which the relative error of the concentration of the first gas component is zero equal to the concentration of the second gas component of the mixed gas, wherein
the concentration correction part corrects the error in the measured concentration of the first gas component with use of the correction coefficient after the change by the correction coefficient changing part and the measured concentration of the second gas component.

4. The gas analysis apparatus according to claim 1, wherein
the first gas analysis part and the second gas analysis part include a detector using an NDIR method.

5. The gas analysis apparatus according to claim 1, wherein
one of the first gas component and the second gas component is carbon monoxide (CO), and
the other of the first gas component and the second gas component is carbon dioxide (CO2).

6. The gas analysis apparatus according to claim 1, wherein
the sample gas is exhaust gas discharged from an internal combustion engine.

7. A gas analysis method using a first gas analysis part adapted to measure concentration of a first gas component in sample gas and a second gas analysis part adapted to measure concentration of a second gas component in the sample gas, the method comprising:

correcting, as the concentration of the second gas component in the sample gas varies, error in the measured concentration of the first gas component obtained by the first gas analysis part on a basis of a correction coefficient, a known concentration of the second gas component contained in mixed gas used for calibrating the first gas analysis part, and the measured concentration of the second gas component obtained by the second gas analysis part, wherein the correction coefficient accounts for error in the measured concentration of the first gas component in the sample gas due to presence of the second gas component in the sample gas; and calibrating the first gas analysis part with mixed gas containing known concentrations of the first gas component and the second gas component.

* * * * *